United States Patent [19]
Broughton et al.

[11] Patent Number: 5,935,151
[45] Date of Patent: Aug. 10, 1999

[54] VERTEBRAL DISTRACTION PUMP

[76] Inventors: Bruce G. Broughton; Raywood C. Weiler, both of SVL Boax 8857, Victorville, Calif. 92392

[21] Appl. No.: 08/573,438

[22] Filed: Dec. 15, 1995

[51] Int. Cl.⁶ .................................................. A61B 17/56
[52] U.S. Cl. ............................................. 606/241; 606/90
[58] Field of Search .................................. 606/61, 86, 90, 606/102, 105, 245, 241, 237; 600/201, 202, 218, 219, 226, 235; 602/19; 623/17; 81/3.7, 485

[56] References Cited

U.S. PATENT DOCUMENTS

| | | | |
|---|---|---|---|
| 3,750,652 | 8/1973 | Sherwin | 606/90 |
| 3,916,907 | 11/1975 | Peterson | 606/90 |
| 4,257,406 | 3/1981 | Schenk | 600/219 |
| 4,898,161 | 2/1990 | Grundei | 606/105 |
| 5,176,129 | 1/1993 | Smith | 600/219 |

FOREIGN PATENT DOCUMENTS

| | | | |
|---|---|---|---|
| 1309976 | 5/1987 | Russian Federation | 606/90 |
| 2198647 | 6/1988 | United Kingdom | 606/90 |

*Primary Examiner*—Guy V. Tucker
*Attorney, Agent, or Firm*—Marshall, O'Toole, Gerstein, Murray & Borun

[57] ABSTRACT

A distraction pump for manipulation of the spinal column and associated bodily structures having a pump body and two arms coupled to the body, one of the arms being movable relative to the other arm. Each arm has displacement means coupled to it. The distraction pump has a handle that is movable between a non-actuated position and an actuated position and actuator means operatively for causing the two displacement means to be moved from a first relative position when the handle is in the non-actuated position to a second relative position when the handle is in the actuated position.

18 Claims, 4 Drawing Sheets

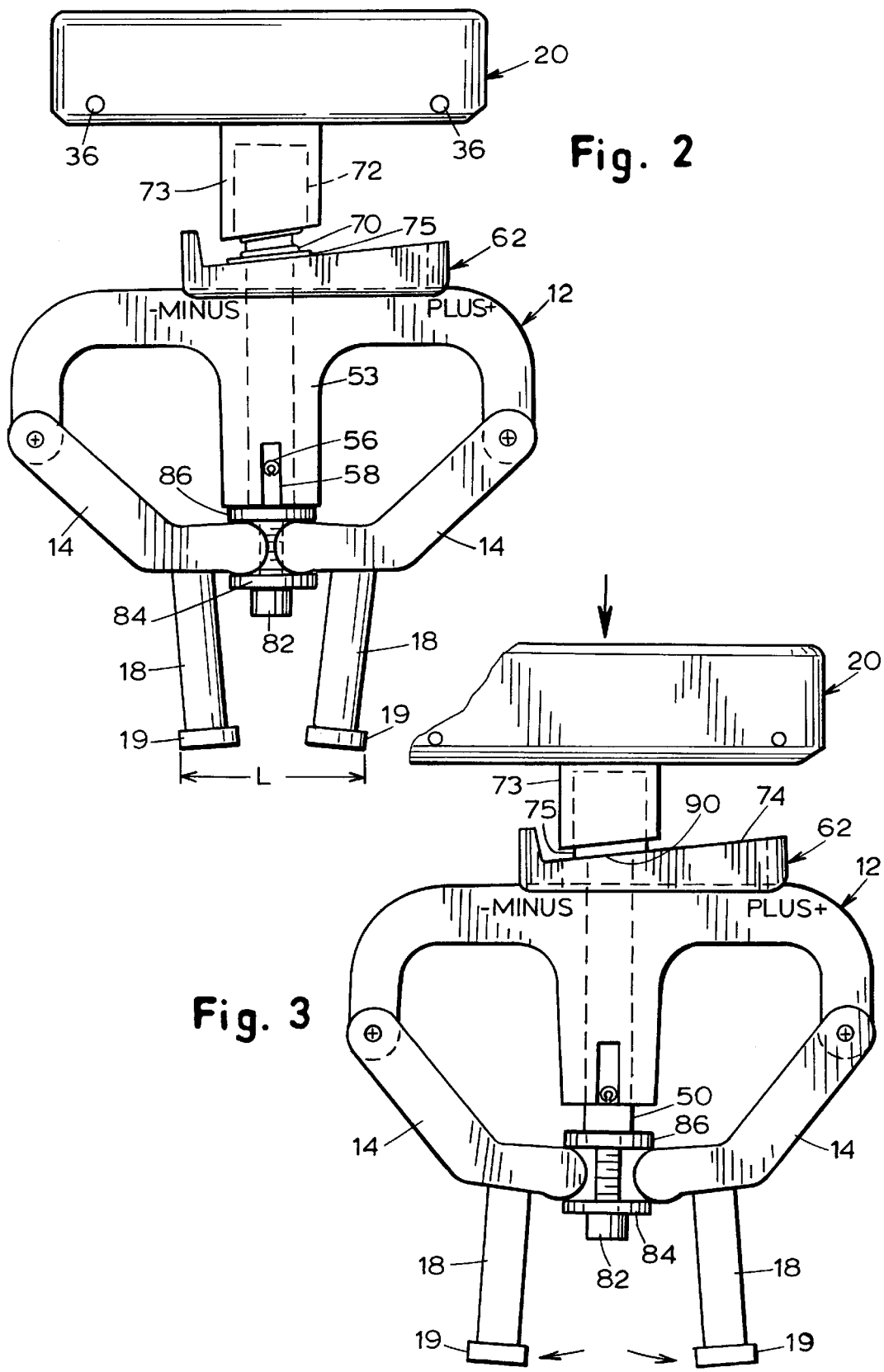

VERTEBRAL DISTRACTION PUMP

BACKGROUND OF THE INVENTION

The present invention is directed to a vertebral distraction pump for manipulation of the spinal column and related bodily structures.

In the case of a herniation of a spinal disc, it is advantageous to induce a slight separation of the posterior portions of the two vertebrae adjacent the herniated disc to induce a hydrostatic pressure change which causes the herniated portion of the disc to be restored to its original anatomical position.

Currently, the options for treating herniated discs are limited. The current treatment options include invasive and non-invasive methods. Invasive measures are exemplified by surgical procedures, while non-invasive methods are those which do not penetrate the skin. Non-invasive measures include manual manipulation of the spinal column via the hands and more complicated methods of manipulation. Current options for treating herniated discs are relatively complicated and/or burdensome.

SUMMARY OF THE INVENTION

The invention is directed to a distraction pump for manipulation of the spinal column and associated bodily structures. In one common application, the distraction pump is used to slightly distract or separate the posterior portions of a pair of vertebrae, such as lumbar or cervical vertebrae, adjacent a herniated disc in order to create a hydrostatic pressure change within the central portion of the disc to cause a suctioning effect which draws the herniated portion of the disc back to its normal anatomical position.

A distraction pump in accordance with the invention has a pump body and two arms coupled to the body, one of the arms being movable relative to the other arm. Each arm has displacement means coupled to it. The distraction pump has a handle that is movable between a non-actuated position and an actuated position and actuator means operatively for causing the two displacement means to be moved from a first relative position when the handle is in the non-actuated position to a second relative position when the handle is in the actuated position.

Each of the displacement means may comprise two rods which extend from the bottom portion of one of the pivot arms. The handle may include a first handle portion, a second handle portion movable relative to the first handle portion, and means for spring-biasing the first handle portion relative to the second handle portion.

The actuator means may include an actuator shaft having a first end attached to the handle, a first disk coupled to the actuator shaft for forcing the first and second arms in a first direction, a second disk coupled to the actuator shaft for forcing the first and second arms in a second direction, and means for spring-biasing the first and second arms to one of the first and second positions.

The distraction pump may also be provided with means for adjusting the distance through which the handle is movable, such as a slidable wedge-shaped adjusting member disposed between the distraction pump body and the handle.

These and other features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 2 is a side view of the distraction pump of FIG. 1 shown in a non-actuated position;

FIG. 3 is a side view of the distraction pump of FIG. 1 shown in an actuated position;

DETAILED DESCRIPTION OF THE PREFERRED EMBODIMENTS

Figure 1:
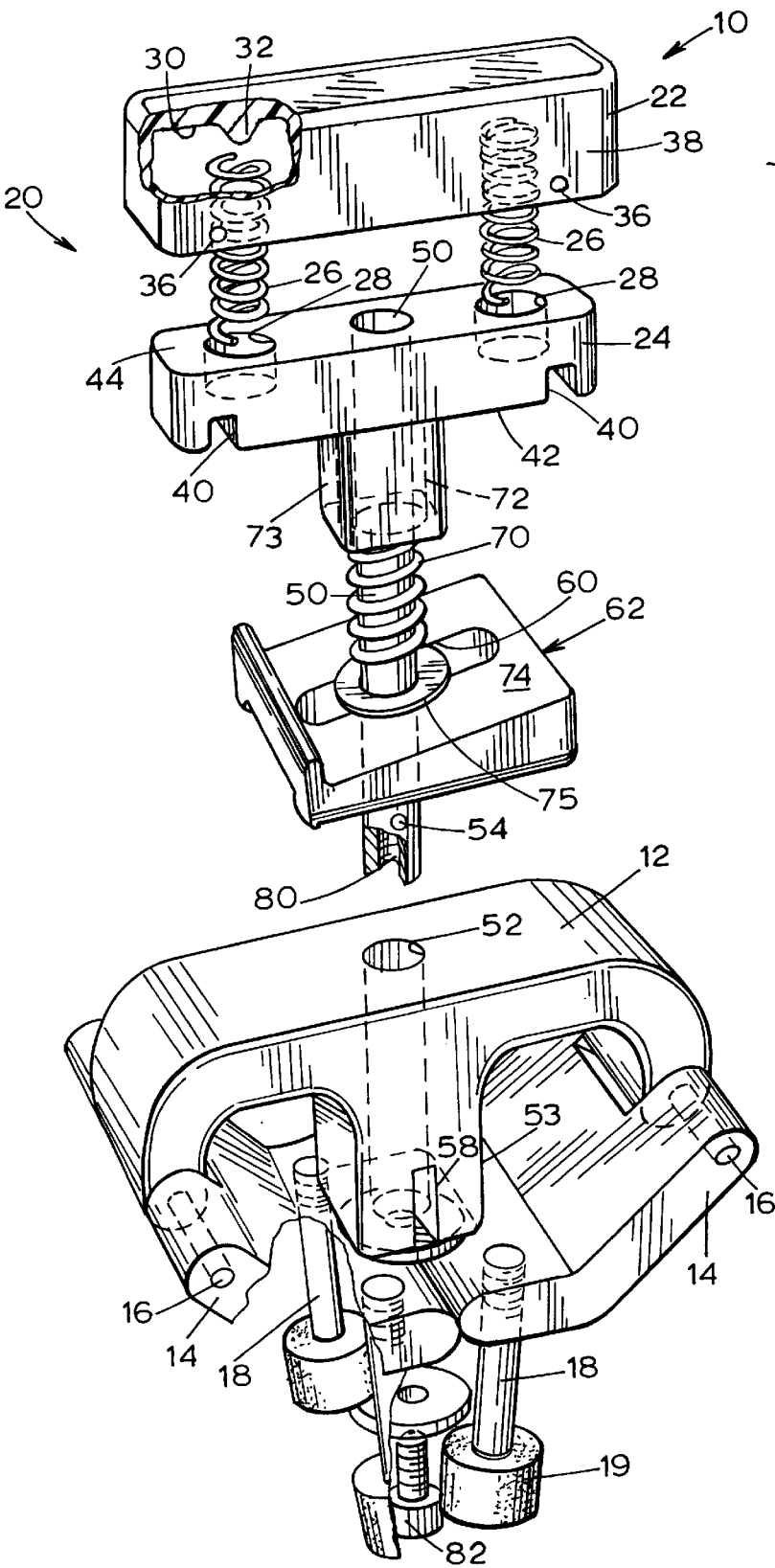
FIG. 1 is an exploded perspective view of one embodiment of a distraction pump in accordance with the invention.

A preferred embodiment of a hand-held distraction pump 10 in accordance with the invention is illustrated in FIG. 1. The distraction pump 10 may be used to restore the herniated portion of a disc located between a pair of adjacent vertebrae to its original anatomical position without having to utilize surgical procedures, which are complicated and burdensome. The distraction pump 10 may be used to cause a separation of the posterior aspects of the superior and inferior vertebrae the disc is between. This creates a hydrostatic pressure change within the central portion of the disc to cause a suctioning effect which draws the herniated portion of the disc back to its normal anatomical position.

Referring to FIG. 1, the pump 10 has a body 12 to which a pair of pivot arms 14 are pivotally attached via a pair of pins 16 which pass through a bore in each pivot arm 14 and a bore in the body 12. Displacement or spreading means in the form of two rods 18 are connected to each of the bottom ends of the pivot arms 14. The bottom end of each rod 18 may be provided with a contact member 19 made of rubber or plastic, for example. The rods 18 may be threadably connected to the pivot arms 14.

The pump 10 has an actuator in the form of a handle 20 which is composed of an upper handle portion 22, in the form of an inverted trough, and a lower handle portion 24 which is spring-biased away from the upper handle portion 22 via a pair of springs 26. The bottom end of each spring 26 is disposed within a respective retaining cup 28 formed in the lower handle portion 24, and the upper end of each spring 26 may be retained in place against an interior upper surface 30 of the upper handle portion 22 via a pair of cone-shaped retaining members 32 integrally formed with the interior upper surface 30 of the upper handle portion 22.

When assembled, the lower handle portion 24 is disposed within the upper handle portion 22 and is retained therein via a pair of retaining pins (not shown), each of which passes through a pair of holes 36 formed in the two side walls 38 of the upper handle portion 22 and a slot 40 formed in a lower surface 42 of the lower handle portion 24. Other retaining means may be used. With the construction just described, the two handle portions 22, 24 are biased apart by the springs 26, but are manually forced together during use of the pump 10 so that an upper surface 44 of the lower handle portion 24 comes into contact with the interior upper surface 30 of the upper handle portion 22.

The pump 10 has an actuator shaft 50 with an upper end which is connected to the lower handle portion 24 and a lower end which passes through a bore 52 formed in a central portion 53 of the pump body 12. The lower end of the actuator shaft 50 has a horizontally disposed bore 54 formed therein to accommodate an alignment pin 56 (FIG. 2), which is disposed within a slot 58 formed in the bottom of the central portion 53 of the pump body 12. Because its orientation is constrained by the slot 58, the alignment pin 56 maintains the orientation of the handle 20 parallel to the pump body 12.

The actuator shaft 50 passes through an elongate slot 60 formed in a slidable adjusting plate 62. The adjusting plate 62 is wedge-shaped, having a thickness which increases at a constant rate from its left side to its right side as shown in FIG. 1. The horizontal distance through which the adjusting plate 62 may be slid is limited by the length of the slot 60 through which the actuator shaft 50 passes.

A spring 70 is disposed about the actuator shaft 50 and within a cylindrical bore 72 formed in a spring enclosure 73 integrally formed with the lower handle portion 24. The lower end of the spring 70 abuts a washer 75 disposed on a top surface 74 of the adjusting plate 62. The spring 70 acts to bias the handle 20 upwards and away from the pump body 12 and also acts to hold the adjusting plate 62 in position by creating frictional force between the adjusting plate 62 and the pump body 12.

The bottom end of the actuator shaft 50 has a vertically disposed internal threaded bore 80 adapted to receive a screw 82. As shown in FIG. 2, the screw 82 supports a lower disk 84 disposed against the bottom surfaces of the ends of the pivot arms 14 and an upper disk 86 disposed against the top surfaces of the ends of the pivot arms 14.

The pump body 12, the pivot arms 14, the rods 18, the upper and lower handle portions 22, 24, the adjusting plate 62, and the disks 84, 86 may be composed of plastic or nylon, for example, while the actuator shaft 50 is preferably composed of steel.

The operation of the displacement pump 10 is described in connection with FIGS. 2 and 3. FIG. 2 illustrates the pump 10 in a non-actuated state in which the spring 70 biases the handle 20 and the actuator shaft 50 to which it is attached to their uppermost position with respect to the pump body 12. The spring 70 cannot force the actuator shaft 50 upwards any further since the abutment of the disk 86 against the pump body 12 prevents further upward movement. When the pump 10 is in its non-actuated position as shown in FIG. 2, the contact members 19 attached to the rods 18 are spaced relatively close together.

The pump 10 may be moved from its non-actuated position to an actuated position by manually forcing the handle 20 downwards. Referring to FIG. 3, the downward movement of the handle 20 forces the actuator shaft 50 downward, which in turn forces the disk 86 and the ends of the pivot arms 14 downward. Consequently, the contact members 19 attached to the rods 18 are moved farther apart. The downward movement of the handle 20 is limited by the abutment of an angled surface 90 of the spring enclosure 73 with the upper angled surface 74 of the adjusting plate 62.

It should be noted that the horizontal position of the adjusting plate 62 changes the lowermost position of the spring enclosure 73 (and thus the maximum distance which the contact members 19 can be spread apart) due to the variable thickness of the adjusting plate 62. The pump body 12 may be provided with visually perceptible indicia or indicating means, such as "–MINUS" on its left-hand side and "PLUS+" on its right-hand side as shown in FIGS. 2 and 3, to indicate to the user the effect of moving the adjusting plate 62 (i.e. when the adjusting plate 62 is slid towards the PLUS+ side, the distance between the contact members 19 is greater when the pump 10 is in its actuated state, and when the adjusting plate 62 is slid towards the –MINUS side, the distance between the contact members 19 is less when the pump 10 is in its actuated state).

When the handle 20 is released by the user, the spring 70 forces the handle 20 and the shaft 50 to which it is attached upwards, thus causing the disk 84 to force the ends of the pivot arms 14 upwards. Consequently, the contact members 19 return to their original position as shown in FIG. 2.

Figure 5:
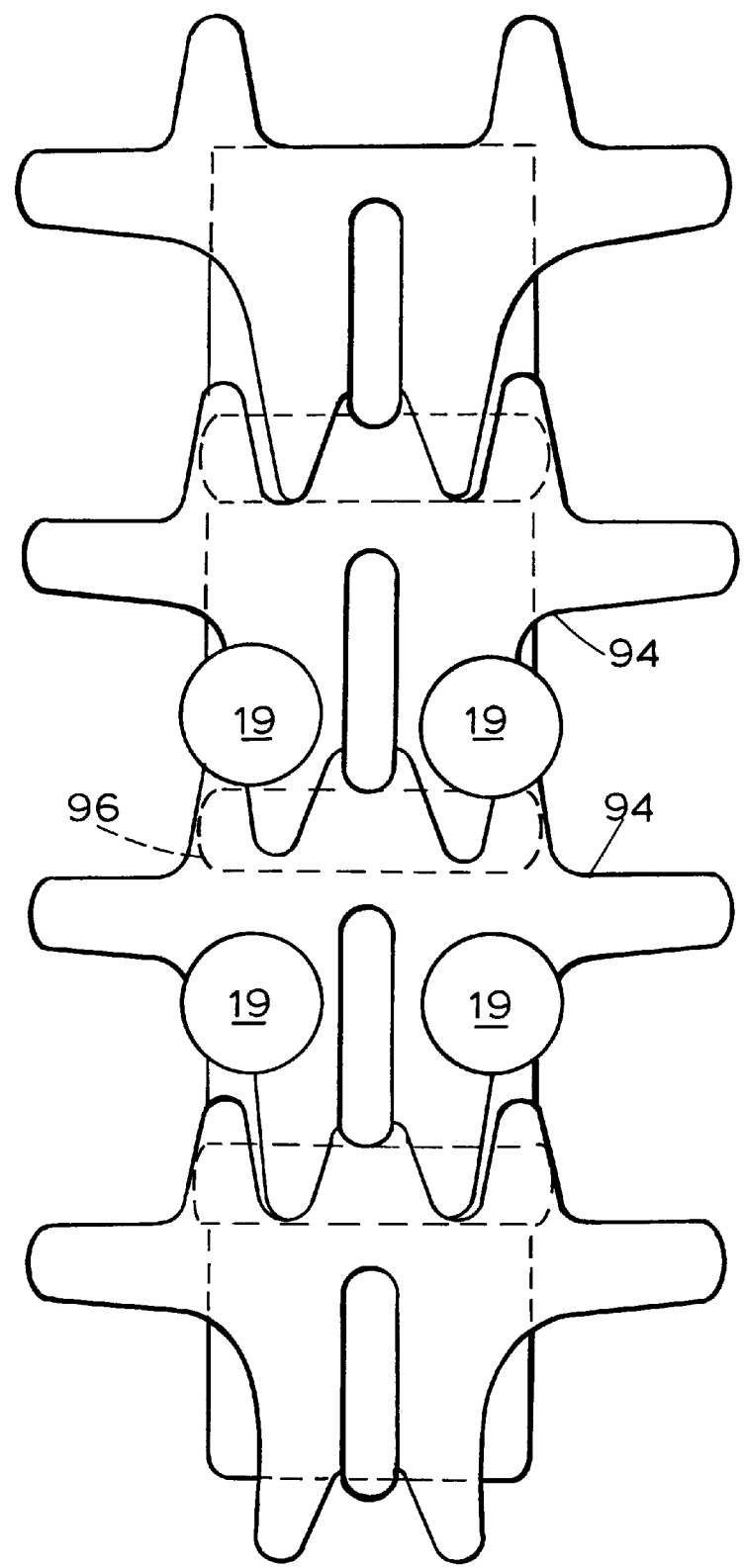
FIG. 5 illustrates the placement of the distraction pump when used to manipulate a pair of adjacent vertebrae.

When used to distract or separate the rear portions of a pair of vertebrae 94 adjacent a disc 96, the initial spacing of the contact members 19 is adjusted so that they occupy the positions relative to the vertebrae 94 as shown in FIG. 5. After such adjustment, the distraction pump 10 is placed against the back (or neck) of the patient, with the user of the pump 10 holding it by placing two fingers on either side of the central body portion 53 and the user's palm over the upper handle portion 22. Then, the user forces the handle portion 22 towards the patient's vertebrae 94 until the springs 26 are totally compressed. With the pump 10 in that position, the contact members 19 make contact with the patient's skin overlying the vertebrae 94 with a force of approximately equal to the compression force of the springs 26.

With the springs 26 compressed, the user then pulls the body portion 12 of the pump 10 away from the patient's vertebrae 94, to cause the contact members 19 to be spread apart, while maintaining the same pressure with the user's palm against the upper handle portion 22. It should be noted that the pulling of the user's fingers away from the patient's vertebrae 94 will not significantly change the force of the contact members 19 against the patient since the pump body 12 merely slides upwards along the actuator shaft 50 while the vertical position of the contact members 19 does not substantially change (compare FIGS. 2 and 3).

When the distraction pump 10 is used to manipulate the back or lumbar vertebrae, the initial spacing L between the outer portions of the contact members 19 (see FIG. 2) with the pump 10 in the non-actuated position may be approximately 1.375 inches. When used for the lumbar vertebrae, the springs 26 in the handle 20 may be selected to provide a total compression force of about ten pounds. It should be appreciated that although the contact members 19 spread apart significantly during actuation of the pump 10, the rear portions of the vertebrae are spread apart by only one or two millimeters since not all of the spreading action is transmitted through the skin to the underlying vertebrae.

Figure 4:
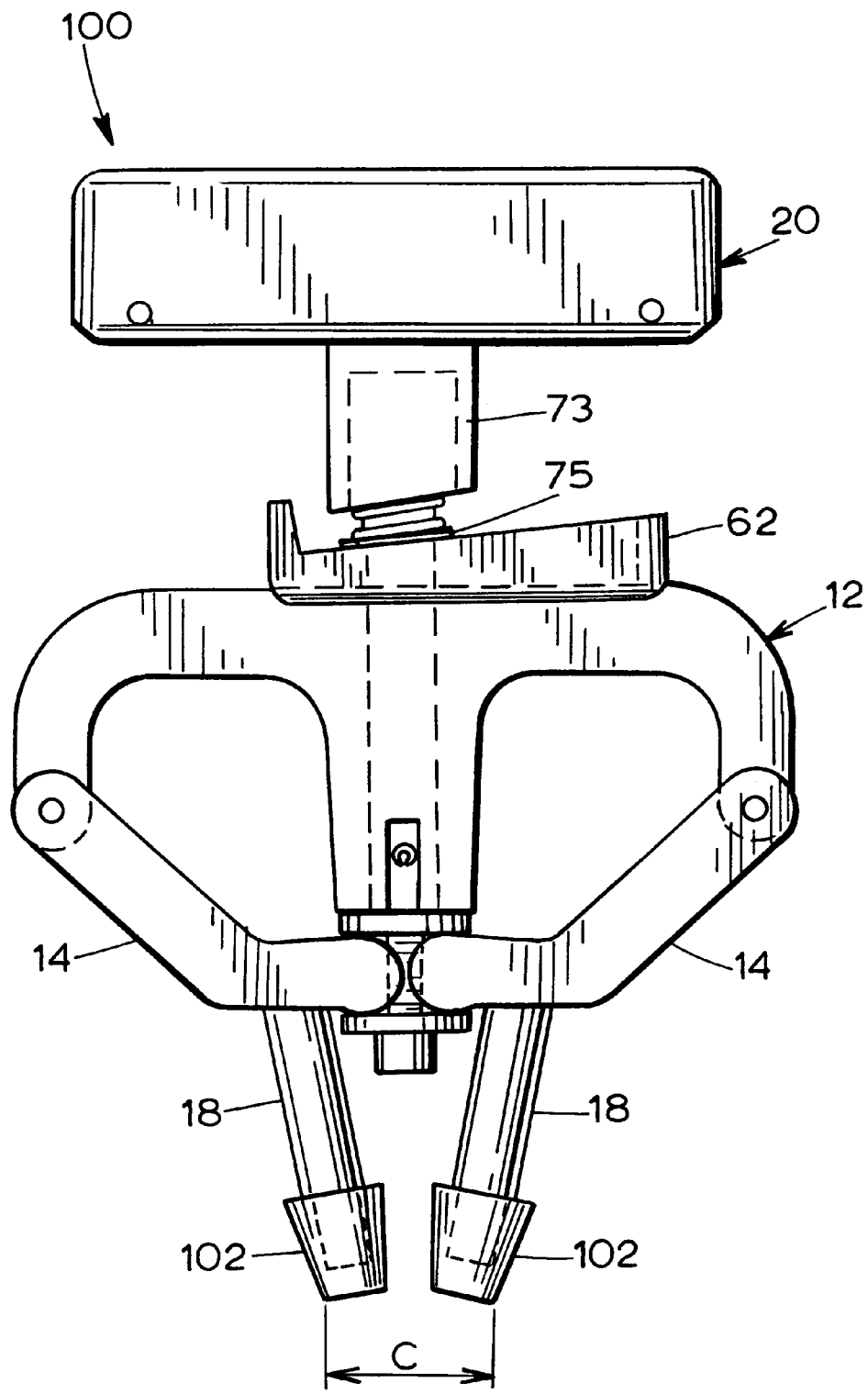
FIG. 4 is a side view of a second embodiment of a distraction pump.

An alternative embodiment of a distraction pump 100 is shown in FIG. 4. The pump 100, which is adapted for use with the neck or cervical vertebrae, differs from the pump 10 of FIGS. 2 and 3 in that the rods 18 are angled, the contact members 102 have a different shape and are spaced apart by a distance C of about 0.85 inches in the non-actuated position, and that the two springs (not shown in FIG. 4) in the handle 20 have a total spring force of about five pounds.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A distraction pump, comprising:
   a body;
   a first pivot arm pivotally coupled to said body;
   a second pivot arm pivotally coupled to said body;
   first displacement means coupled to said first pivot arm, said first displacement means comprising two rods which extend from said first pivot arm;
   second displacement means coupled to said second pivot arm, said second displacement means comprising two rods which extend from said second pivot arm;

a handle movable through a displacement distance from a non-actuated position to an actuated position; and actuator means operatively coupled between said handle and said first and second pivot arms for causing said first and second displacement means to be moved from a first relative position when said handle is in said non-actuated position to a second relative position when said handle is in said actuated position, said actuator means comprising:
- an actuator shaft having a first end attached to said handle and a second end;
- a first disk coupled to said actuator shaft for forcing said first and second pivot arms in a first direction;
- a second disk coupled to said actuator shaft for forcing said first and second pivot arms in a second direction;
- a movable wedge-shaped member for adjusting said displacement distance through which said handle is movable; and
- means for spring-biasing said first and second pivot arms to one of said first and second positions.

2. A distraction pump as defined in claim 1 wherein said handle comprises:
- a first handle portion;
- a second handle portion movable relative to said first handle portion; and
- means for spring-biasing said first handle portion relative to said second handle portion.

3. A distraction pump, comprising:
- a body;
- a first pivot arm pivotally coupled to said body;
- a second pivot arm pivotally coupled to said body;
- first displacement means coupled to said first pivot arm;
- second displacement means coupled to said second pivot arm;
- a first contact member connected to said first displacement means, said first contact member being adapted to noninvasively manipulate a vertebra of a patient without passing through the skin of the patient;
- a second contact member connected to said second displacement means, said second contact member being adapted to noninvasively manipulate a vertebra of the patient without passing through the skin of the patient;
- a handle movable from a non-actuated position to an actuated position; and
- actuator means operatively coupled between said handle and said first and second pivot arms for causing said first and second displacement means to be moved in a spreading direction from a first relative position when said handle is in said non-actuated position to a second relative position when said handle is in said actuated position, said actuator means including a spring compressible in a direction generally perpendicular to said spreading direction for biasing said first and second displacement means to their first relative position.

4. A distraction pump as defined in claim 3 wherein each of said first and second displacement means comprises at least one rod which extends from one of said pivot arms.

5. A distraction pump as defined in claim 3 wherein each of said first and second displacement means comprises two rods which extend from one of said pivot arms.

6. A distraction pump as defined in claim 3 wherein said actuator means comprises an actuator shaft having a first end attached to said handle and a second end operatively coupled to said first and second pivot arms.

7. A distraction pump as defined in claim 3 wherein said actuator means comprises:
- an actuator shaft having a first end attached to said handle and a second end;
- a first disk coupled to said actuator shaft for forcing said first and second pivot arms in a first direction; and
- a second disk coupled to said actuator shaft for forcing said first and second pivot arms in a second direction.

8. A distraction pump as defined in claim 3 wherein said actuator means comprises means for causing said first and second displacement means to be moved from said first relative position to said second relative position when said handle is moved through a displacement distance, said distraction pump additionally comprising means for adjusting said displacement distance through which said handle is movable.

9. A distraction pump, comprising:
- a body;
- a first pivot arm pivotally coupled to said body;
- a second pivot arm pivotally coupled to said body;
- first displacement means coupled to said first pivot arm;
- second displacement means coupled to said second pivot arm;
- a handle movable from a non-actuated position to an actuated position; and
- actuator means operatively coupled between said handle and said first and second pivot arms for causing said first and second displacement means to be moved from a first relative position when said handle is in said non-actuated position to a second relative position when said handle is in said actuated position,
- wherein said actuator means comprises means for causing said first and second displacement means to be moved from said first relative position to said second relative position when said handle is moved through a displacement distance, said distraction pump additionally comprising means for adjusting said displacement distance through which said handle is movable, and
- wherein said adjusting means comprises a movable wedge-shaped member disposed between said body and said handle.

10. A distraction pump, comprising:
- a body;
- a first pivot arm pivotally coupled to said body;
- a second pivot arm pivotally coupled to said body;
- first displacement means coupled to said first pivot arm;
- second displacement means coupled to said second pivot arm;
- a handle movable from a non-actuated position to an actuated position; and
- actuator means operatively coupled between said handle and said first and second pivot arms for causing said first and second displacement means to be moved from a first relative position when said handle is in said non-actuated position to a second relative position when said handle is in said actuated position, wherein said handle comprises:
  - a first handle portion;
  - a second handle portion movable relative to said first handle portion; and
  - means for spring-biasing said first handle portion relative to said second handle portion.

11. A distraction pump, comprising:
- a body;

a first arm coupled to said body;

a second arm coupled to said body, said first arm being movable relative to said second arm;

first displacement means coupled to said first arm;

second displacement means coupled to said second arm;

a first contact member connected to said first displacement means, said first contact member being adapted to noninvasively manipulate a vertebra of a patient without passing through the skin of the patient;

a second contact member connected to said second displacement means, said second contact member being adapted to noninvasively manipulate a vertebra of the patient without passing through the skin of the patient;

an actuator movable from a non-actuated position to an actuated position; and actuator means operatively coupled to said actuator and said first and second arms for causing said first and second displacement means to be moved from a first relative position when said actuator is in said non-actuated position to a second relative position when said actuator is in said actuated position, said actuator means including a spring for biasing said first and second displacement means to said first relative position.

12. A distraction pump as defined in claim 11 wherein each of said first and second displacement means comprises two rods which extend from one of said arms.

13. A distraction pump as defined in claim 11 wherein said actuator means comprises an actuator shaft having a first end attached to said actuator and a second end operatively coupled to said first and second arms.

14. A distraction pump as defined in claim 11 wherein said actuator means comprises:

an actuator shaft having a first end attached to said actuator and a second end;

a first disk coupled to said actuator shaft for forcing said first and second arms in a first direction; and a second disk coupled to said actuator shaft for forcing said first and second arms in a second direction.

15. A distraction pump as defined in claim 11 wherein said actuator means comprises means for causing said first and second displacement means to be moved from said first relative position said second relative position when said actuator is moved through a displacement distance, said distraction pump additionally comprising means for adjusting said displacement distance through which said actuator is movable.

16. A distraction pump as defined in claim 11 wherein each of said first and second displacement means comprises means for displacing a pair of adjacent vertebrae away from each other.

17. A distraction pump, comprising:

a body;

a first arm coupled to said body;

a second arm coupled to said body, said first arm being movable relative to said second arm;

first displacement means coupled to said first arm;

second displacement means coupled to said second arm;

an actuator movable from a non-actuated position to an actuated position; and actuator means operatively coupled to said actuator and said first and second arms for causing said first and second displacement means to be moved from a first relative position when said actuator is in said non-actuated position to a second relative position when said actuator is in said actuated position, wherein said adjusting means comprises a movable wedge-shaped member disposed between said body and said actuator.

18. A distraction pump, comprising:

a body;

a first arm coupled to said body;

a second arm coupled to said body, said first arm being movable relative to said second arm;

first displacement means coupled to said first arm;

second displacement means coupled to said second arm;

an actuator movable from a non-actuated position to an actuated position; and actuator means operatively coupled to said actuator and said first and second arms for causing said first and second displacement means to be moved from a first relative position when said actuator is in said non-actuated position to a second relative position when said actuator is in said actuated position, wherein said actuator comprises:

a first handle portion;

a second handle portion movable relative to said first handle portion; and means for spring-biasing said first handle portion relative to said second handle portion.

* * * * *